US008841452B1

(12) United States Patent
De Faveri et al.

(10) Patent No.: US 8,841,452 B1
(45) Date of Patent: Sep. 23, 2014

(54) PROCESS FOR RECOVERY OF NALMEFENE HYDROCHLORIDE

(71) Applicant: H. Lundbeck A/S, Valby (DK)

(72) Inventors: Carla De Faveri, Farra di Soligo (IT); Mariano Stivanello, Schio (IT)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/294,707

(22) PCT Filed: Dec. 6, 2012

(86) PCT No.: PCT/EP2012/074623
§ 371 (c)(1),
(2), (4) Date: Jun. 3, 2014

(87) PCT Pub. No.: WO2013/083685
PCT Pub. Date: Jun. 13, 2013

Related U.S. Application Data

(60) Provisional application No. 61/567,148, filed on Dec. 6, 2011.

(30) Foreign Application Priority Data

Dec. 6, 2011 (DK) .................................. 2011 00948

(51) Int. Cl.
*C07D 489/08* (2006.01)
*C07D 489/02* (2006.01)

(52) U.S. Cl.
CPC .................................... *C07D 489/08* (2013.01)
USPC .............................................. 546/44; 546/45

(58) Field of Classification Search
USPC ....................................................... 546/44, 45
See application file for complete search history.

(56) References Cited

U.S. PATENT DOCUMENTS

| 3,814,768 | A | 6/1974 | Fishman |
| 3,896,226 | A | 7/1975 | Fishman |
| 4,535,157 | A | 8/1985 | Meltzer et al. |
| 4,751,307 | A | 6/1988 | White |
| 2008/0312442 | A1 | 12/2008 | Buehler et al. |
| 2011/0251228 | A1 | 10/2011 | Lopez de Diego et al. |

FOREIGN PATENT DOCUMENTS

| EP | 2121669 B1 | 9/2012 |
| WO | 2010/136039 A1 | 12/2010 |

OTHER PUBLICATIONS

Elliot F. Hahn et al., 1975, "Narcotic Antagonists. 4. Carbon-6 Derivatives of N-Substituted Noroxymorphones as Narcotic Antagonists", Journal of Medicinal Chemistry, vol. 18, No. 3, pp. 259-262.

*Primary Examiner* — Charanjit Aulakh
(74) *Attorney, Agent, or Firm* — Mary Catherine Di Nunzio

(57) ABSTRACT

The present invention relates to an improved process for recovery of nalmefene hydrochloride[17-(cyclopropylmethyl)-4,5-alpha-epoxy-6-methylenemorphinan-3,14-diol hydrochloride] from an aqueous composition containing nalmefene and certain impurities.

19 Claims, No Drawings

PROCESS FOR RECOVERY OF NALMEFENE HYDROCHLORIDE

CROSS-REFERENCE TO RELATED APPLICATIONS

This present application is a National Stage Application which claims priority of International Application No. PCT/EP2012/074623, filed Dec. 6, 2012, which claims priority of U.S. Provisional Application No. 61/567,148 filed Dec. 6, 2011 and Danish Application No. PA201100948, filed Dec. 6, 2011. Each of these applications is hereby incorporated by reference in its entirety.

FIELD OF THE INVENTION

The present invention relates to an improved process for recovery of nalmefene hydrochloride[17-(cyclopropylmethyl)-4,5-alpha-epoxy-6-methylenemorphinan-3,14-diol hydrochloride] from an aqueous composition containing nalmefene and certain impurities.

BACKGROUND OF THE INVENTION

Nalmefene is a known opioid system modulator, with a distinct μ, δ, and κ receptor profile, which can inhibit pharmacological effects of both administered opioid agonists and endogenous agonists derived from the opioid system. The clinical usefulness of nalmefene comes from its ability to promptly (and selectively) reverse the effects of these opioid agonists.

Nalmefene has been developed as the hydrochloride salt for use in the management of alcohol dependency, where it has shown good effect at doses of 10 to 40 mg taken when the patient experiences a craving for alcohol (Karhuvaara et al., *Alcohol. Clin. Exp. Res.*, (2007), Vol. 31 (7): 1179-1187; Trial watch: Nalmefene reduces alcohol use in phase III trial, *Nature reviews Drug discovery* (2011) Vol. 10 (8): 566). Additionally, nalmefene has also been investigated for the treatment of other addictions such as pathological gambling and addiction to shopping.

Nalmefene is an opiate derivative structurally related to the opiate antagonist naltrexone. Advantages of nalmefene compared to naltrexone include longer half-life, higher oral bioavailability and the absence of dose-dependent liver toxicity.

Nalmefene can be produced from naltrexone by the Wittig reaction. Methods for preparation of nalmefene from naltrexone by the Wittig reaction has been described by Hahn et al., (*J. Med. Chem.* (1975) Vol. 18: 259-262, Mallinckrodt (U.S. Pat. No. 4,751,307), Meltzner et al., (U.S. Pat. No. 4,535,157) and by H. Lundbeck (WO 2010/136039). By using the abovementioned methods, the free base of nalmefene is obtained, which subsequently can be converted into the hydrochloride salt by use of conventional methods.

WO 2010/063292 discloses nalmefene hydrochloride dihydrate and methods for its manufacturing. The dihydrate form is the preferred crystalline form of nalmefene hydrochloride because its non-hygroscopic properties improve the API stability under storage and formulation conditions. Nalmefene hydrochloride dihydrate can be manufactured by re-slurry or by re-crystallization of nalmefene hydrochloride from an aqueous solution as disclosed in WO 2010/063292. By the re-slurry method disclosed in WO 2010/063292, nalmefene hydrochloride is mixed with an aqueous solution to obtain a suspension, whereupon the mixture is stirred and the solid is isolated. By the re-crystallization method, nalmefene hydrochloride is mixed with an aqueous solution and heated to obtain a substantially homogenous solution whereupon the solution is cooled and subsequently seeded with nalmefene hydrochloride whereupon the formed solid is isolated.

Due to the solubility of nalmefene hydrochloride in water, a considerable amount of the product is lost in the mother liquor from said re-slurry and re-crystallization methods as illustrated by below reaction scheme. Up to 25-35% of the nalmefene hydrochloride may remain in the mother liquor.

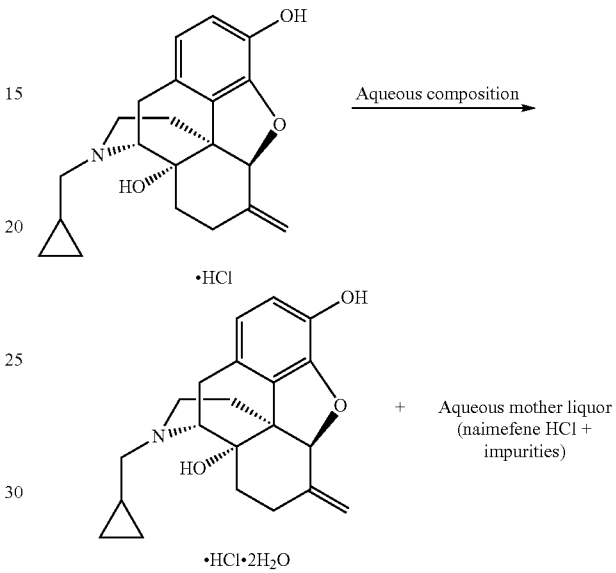

Thus, methods to improve recovery from the mother liquor will greatly improve process yields and thus lower overall production costs.

Furthermore, certain impurities are enriched in the mother liquor. Impurities in the mother liquor can be divided into two groups. Morphinan related compounds, mainly naltrexone, and phosphorous by-products generated when nalmefene has been synthesized from naltrexone by the Wittig reaction. Particularly naltrexone, the synthetic precursor of nalmefene is difficult to remove selectively in the recovery process since naltrexone has chemical properties very similar to those of nalmefene.

One process for recovery of un-precipitated nalmefene hydrochloride from the mother liquor of the re-slurry and re-crystallization methods is disclosed in WO 2010/063292. The recovery process of WO 2010/063292 comprises basification of the mother liquor followed by extracting with an organic solvent. The organic solvent is isolated and nalmefene is precipitated from the organic solvent by acidification with hydrogen chloride.

There is a need to find new and improved processes for recovery of nalmefene hydrochloride from aqueous compositions containing nalmefene and certain impurities, such as from mother liquors obtained from methods of preparation of nalmefene hydrochloride dihydrate. In particular there is a need for new and improved processes giving nalmefene hydrochloride in a highly pure form.

SUMMARY OF THE INVENTION

The present invention relates to an improved process for recovery of nalmefene hydrochloride from an aqueous composition containing nalmefene and certain impurities. In one embodiment, the aqueous composition comprises a mother liquor arisen from recrystallisation or re-slurry of nalmefene hydrochloride in water.

In one embodiment, the invention relates to a process for recovery of nalmefene hydrochloride from an aqueous composition containing nalmefene hydrochloride and naltrexone, said process comprising isolating nalmefene hydrochloride from an aqueous suspension comprising naltrexone bisulfite adduct and solid nalmefene hydrochloride.

In one embodiment, the invention relates to a process for the preparation of nalmefene hydrochloride dihydrate or nalmefene hydrochloride monohydrate, wherein said process includes recovering nalmefene hydrochloride by a process of the invention.

In one embodiment, the invention relates to a compound represented by the formula

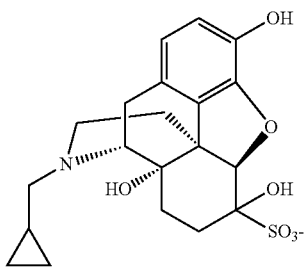

DEFINITIONS

Throughout the description, the terms "nalmefene" and "naltrexone" are intended to include any forms of the compounds, such as the free base and pharmaceutically acceptable salts. The free base and pharmaceutically acceptable salts include anhydrous forms and solvated forms such as hydrates. The anhydrous forms and the solvates include amorphous and crystalline forms.

In the present context, the terms "bisulfite salt" and "suitable salt generating the bisulfite anion in an aqueous medium" are intended to indicate salts generating the hydrogensulfite anion $HSO_3^-$ when dissolved in an aqueous media. Examples include, but are not limited to, sodium bisulfite, potassium bisulfite and calcium bisulfite. Particular mention is made of sodium bisulfite.

In the present context, the term "chemically pure" has its normal meaning within the art. Accordingly, an obtained compound which is at least 98% chemically pure comprises at most 2% chemical impurities. The chemical purity may be determined e.g. by HPLC. In the present context purity is determined by % HPLC area.

In the present context, the term "aqueous suspension" indicates an aqueous heterogeneous mixture containing solid particles and dissolved material. Particular mention is made of an aqueous suspension containing nalmefene hydrochloride which is partly on solid phase and naltrexone bisulfite adduct which is mainly in solution.

In the present context, the term "aqueous solution" indicates an aqueous homogeneous mixture composed of only one phase. In aqueous solutions of the present invention one or more solutes are dissolved in the aqueous solvent. Particular mention is made of an aqueous solution containing dissolved nalmefene hydrochloride and certain impurities including naltrexone.

In the present context, the term "aqueous composition" indicates an aqueous composition that can be either an aqueous suspension or an aqueous solution. In one embodiment, an "aqueous composition" of the present invention comprises nalmefene hydrochloride and naltrexone wherein said nalmefene hydrochloride and/or naltrexone can be on solid phase and/or in solution. In a particular embodiment, the "aqueous composition" comprises a mother liquor containing nalmefene hydrochloride and certain impurities including naltrexone.

In the present context, the term "mother liquor" indicates the solution which is left over after separation of solids from a suspension. In the examples 1-4 of the present invention, the mother liquor is an aqueous solution which has been obtained by the re-slurry and/or the recrystallization methods for preparation of nalmefene hydrochloride dihydrate disclosed in WO 2010/063292.

In the present context, the term "residue of evaporation" indicates the amount of residue that would be obtained after removing completely the solvent from a mixture. In the examples of the present invention, "Residue of evaporation" comprises nalmefene hydrochloride and impurities such as naltrexone and phosphorous by-products.

In the present context, the term "phosphorous by-products" indicates phosphorous compounds, mainly phosphine oxides, which might be present when nalmefene has been synthesized from naltrexone by the Wittig reaction. Particular mention is made of triphenylphosphine oxide and methyl-diphenylphosphine oxide.

DETAILED DESCRIPTION OF THE INVENTION

The inventors of the present invention have found an improved process for recovery of nalmefene hydrochloride [17-(cyclopropylmethyl)-4,5-alpha-epoxy-6-methylenemorphinan-3,14-diol hydrochloride] from aqueous compositions comprising nalmefene and certain impurities including naltrexone. The process is particularly useful for recovery of nalmefene hydrochloride from a mother liquor of the re-slurry or the re-crystallization methods for preparation of nalmefene hydrochloride dihydrate disclosed in WO 2010/063292. The process can also be used for recovery of nalmefene hydrochloride from an aqueous mother liquor obtained from any other crystallization method of nalmefene hydrochloride e.g. obtained from preparation of nalmefene hydrochloride monohydrate. The recovery process of the present invention comprises several advantages such as selective removal of naltrexone which is the main nalmefene related impurity present in the mother liquor; recovery of nalmefene hydrochloride from mother liquor and isolation of nalmefene hydrochloride in highly pure form.

The inventors have found that naltrexone can be efficiently removed by formation of its bisulfite adduct according to the following reaction scheme:

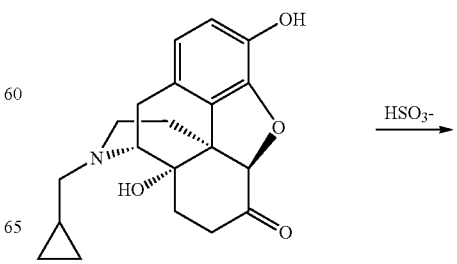

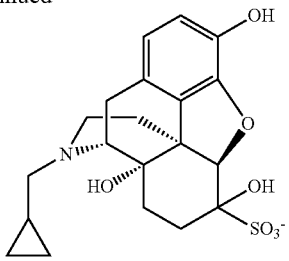

Since only compounds containing a carbonyl moiety can react with the bisulfite anion nalmefene cannot undergo to such reaction. The bisulfite adduct of naltrexone is more soluble than naltrexone itself thus permitting the removal of this impurity.

In brief, the process for the recovery of nalmefene hydrochloride from the aqueous composition comprises isolating nalmefene from an aqueous suspension, wherein said suspension comprises naltrexone bisulfite adduct and solid nalmefene hydrochloride.

In one embodiment, the invention comprises the steps (b)-(e). Step (b) comprises concentrating the aqueous composition. This step is particularly relevant if the aqueous composition initially is an aqueous solution e.g. if the aqueous composition is a mother liquor. By step (b) the aqueous composition is brought from solution state to suspension state. In a particular embodiment the aqueous composition is concentrated under vacuum.

Step (c) comprises mixing the aqueous composition with a bisulfite salt or a suitable salt generating the bisulfite anion in an aqueous medium. In a particular embodiment the bisulfite salt is sodium bisulfite.

The steps (b) and (c) can be performed simultaneously and/or sequentially in any order. In a preferred embodiment, steps (b) and (c) are performed sequentially starting with step (b) followed by step (c). The suspension obtained in step (b) can optionally be diluted.

In one embodiment, wherein steps (b) and (c) are performed sequentially starting with step (b) followed by step (c), the reaction mixture obtained in step (c) is maintained at about 60-65° C. for at least 1 hour to optimize the formation of the bisulfite adduct of naltrexone which remains dissolved in the liquid phase.

In step (d) the suspension is cooled. In step (e) nalmefene hydrochloride is isolated from the suspension. In one embodiment, nalmefene hydrochloride is isolated by filtration and washed with an organic solvent and/or water. Organic solvents suitable for this step include e.g. halogenated hydrocarbons, esters, ethers, ketones and aromatic hydrocarbons. In a further embodiment the process comprises subsequently step (f) wherein the solid is washed with one or more suitable organic solvents e.g. selected from dichloromethane and acetone.

Phosphine oxides (mainly triphenylphosphine oxide) constitute another group of impurities which might be present in the mother liquor if nalmefene has been synthesized from naltrexone by the Wittig reaction. Said phosphine oxides can be selectively removed from the mother liquor by extraction with an organic solvent.

Accordingly, in a further embodiment, wherein the aqueous composition is an aqueous solution, the process involves an initial step, (a) wherein the aqueous composition is extracted with a suitable organic solvent, e.g. a solvent selected from the group of halogenated hydrocarbons, esters, ethers, aromatic hydrocarbons and ketones. In a particular embodiment, the aqueous composition is extracted with dichloromethane. Upon extraction the aqueous phase is isolated and treated e.g. according to steps (b)-(e).

In one embodiment, said aqueous composition comprises a mother liquor obtained from a method of preparation of nalmefene hydrochloride dihydrate, such as the re-slurry or the re-crystallization method disclosed for preparation of nalmefene hydrochloride dihydrate in WO 2010/063292 e.g. exemplified by examples 1, 3, 5 and 6 of WO 2010/063292.

In another embodiment, said aqueous composition comprises a mother liquor obtained from a method of preparation of nalmefene hydrochloride monohydrate, e.g. exemplified by example 2 of WO 2010/063292.

Nalmefene hydrochloride obtained according to the present invention may be further treated e.g. according to the re-crystallization and re-slurry processes disclosed in WO 2010/063292 to obtain the corresponding dihydrate, or nalmefene hydrochloride obtained according to the present invention may be further treated to obtain the corresponding monohydrate.

Said nalmefene hydrochloride dihydrate or monohydrate may be used in the preparation of pharmaceutical compositions. Said pharmaceutical compositions may further comprise at least one pharmaceutically acceptable excipient, carrier and/or diluent, and may be in a solid dosage form, such as a tablet, for oral administration. In one embodiment, the invention relates to such pharmaceutical composition.

Methods for the preparation of solid pharmaceutical preparations are well known in the art. See, e.g., Remington: The Science and Practice of Pharmacy, 21st ed., Lippincott Williams & Wilkins (2005). Solid preparations, such as tablets, may be prepared by mixing the active ingredients with an ordinary carrier, such as an adjuvant and/or diluent, and subsequently compressing the mixture in a tabletting machine. Non-limiting examples of adjuvants and/or diluents include: corn starch, lactose, talcum, magnesium stearate, gelatine, lactose, gums, and the like. Any other appropriate adjuvant or additive such as colourings, aroma, and preservatives may also be used provided that they are compatible with the active ingredients. The pharmaceutical compositions of the invention thus typically comprise an effective amount of nalmefene hydrochloride and one or more pharmaceutically acceptable carriers.

Nalmefene hydrochloride dihydrate or monohydrate obtained according to the present invention may be administered in any suitable way, e.g. orally or parenterally, and it may be presented in any suitable form for such administration, e.g., in the form of tablets, capsules, powders, syrups or solutions or dispersions for injection. In one embodiment, the pharmaceutical composition will comprise nalmefene in a therapeutically effective amount. The term "therapeutically effective amount" refers to the amount/dose of a compound or pharmaceutical composition that is sufficient to produce an effective response (i.e., a biological or medical response of a tissue, system, animal or human sought by a researcher, veterinarian, medical doctor or other clinician) upon administration to a patient. The "therapeutically effective amount" will vary depending on, inter alia, the disease and its severity, and on the age, weight, physical condition and responsiveness of the patient to be treated. Furthermore, the "therapeutically effective amount" may vary if the compound of the invention is combined with one or more compounds: In such a case the amount of a given compound might be lower, such as a sub-effective amount.

Preferably, the amount of nalmefene hydrochloride in a pharmaceutical composition in unit dosage form is from about 10 mg to about 100 mg, such as from about 10 mg to about 60 mg, e.g. from about 10 mg to about 40 mg, or about 20 mg.

In particular, it is envisaged that a pharmaceutical composition comprising nalmefene hydrochloride obtained by a process of the present invention may be used for reduction of alcohol consumption in patients with alcohol dependence. In another embodiment, a composition comprising nalmefene hydrochloride obtained by a process of the present invention may be used for the manufacture of a medicament for reduction of alcohol consumption in patients with alcohol dependence. In another embodiment, the invention relates to a method for treating alcohol dependency, comprising administering a therapeutically effective amount of nalmefene hydrochloride obtained by a process of the present invention to a patient in the need thereof.

The term "alcohol dependency" is a commonly known term for a skilled person. In the revised 4th edition of the Diagnostic and Statistical Manual of Mental Disorders (DSM-IVTR) (*Diagnostic and Statistical Manual of Mental Disorders*, 4th edition text revision, American Psychiatric Publishing, 2000), the term "alcohol dependency" is defined as the presence of three or more of the seven areas of life impairment related to alcohol in the same 12-month period. These impairments include tolerance, evidence of a withdrawal syndrome when alcohol is discontinued or intake is decreased, potential interference with life functioning associated with spending a great deal of time using alcohol, and returning to use despite evidence of physical or psychological problems.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

EMBODIMENTS ACCORDING TO THE INVENTION

In the following, embodiments of the invention are disclosed. The first embodiment is denoted E1, the second embodiment is denoted E2 and so forth.

E1. A process for recovery of nalmefene hydrochloride from an aqueous composition containing nalmefene hydrochloride and naltrexone, said process comprising the step of isolating nalmefene hydrochloride from an aqueous suspension comprising naltrexone bisulfite adduct and solid nalmefene hydrochloride.

E2. The process according to embodiment 1, wherein said aqueous composition is an aqueous solution.

E3. A process according to any of embodiments 1-2 comprising the following steps;
 (b) concentrating the aqueous composition;
 (c) mixing the aqueous composition with a bisulfite salt or with a suitable salt generating the bisulfite anion in an aqueous medium, wherein steps (b) and (c) can be performed simultaneously and/or sequentially in any order,
 (d) cooling the mixture obtained from steps (b) and (c),
 (e) isolating the solid from the mixture obtained in step (d), to obtain nalmefene hydrochloride E4. The process according to embodiment 3, wherein steps (b) and (c) are performed simultaneously.

E5. The process according to embodiment 3, wherein steps (b) and (c) are performed sequentially starting with step (c) followed by step (b).

E6. The process according to embodiment 3, wherein steps (b) and (c) are performed sequentially starting with step (b) followed by step (c).

E7. The process according to embodiment 6, wherein step (b) is followed by step (b') which is performed prior to step (c);
 (b') diluting the aqueous composition with water.

E8. The process according to any of embodiments 3-7, comprising the initial step (a) which is performed prior to steps (b) and (c);
 (a) extracting the aqueous composition with an organic solvent followed by isolation of the aqueous layer,
 wherein the aqueous composition of step (b) or (c) comprises the aqueous layer isolated from step (a).

E9. The process according to embodiment 8, wherein step (a) is repeated 1-3 times.

E10. The process according to any of embodiments 8-9, wherein the organic solvent in step (a) is dichloromethane.

E11. The process according to any of embodiments 3-10, wherein the concentration in step (b) is performed by vacuum distillation.

E12. The process according to any of embodiments 3-11, wherein the bisulfite salt in step (c) is sodium bisulfite.

E13. The process according to any of embodiments 6-12, wherein the mixture obtained in step (c) is maintained in a temperature range of about 20-100° C. for at least 1 hour.

E14. The process according to embodiment 13, wherein the mixture obtained in step (c) is maintained in a temperature range of about 20-100° C. in a time range of about 1-6 hours.

E15. The process according to embodiment 14, wherein said temperature range is about 20-80° C. such as about 50-70° C. such as about 50-55° C. or about 55-60° C. or about 60-65° C. or about 65-70° C.

E16. The process according to any of embodiments 14-15, wherein said time range is about 2-5 hours such as about 2.5-4.5 hours such as about 3-4 hours.

E17. The process according to any of embodiments 3-16, wherein the cooling in step (d) is performed until the temperature is in the range of 0-20° C., such as in the range of 0-10° C., such as in the range of 0-5° C.

E18. The process according to any of embodiments 3-17, wherein the isolation of the formed solid in step (e) is performed by filtration.

E19. The process according to any of embodiments 3-18 followed by the step; (f) washing the solid obtained in step (e) with one or more suitable organic solvents.

E20. The process according to embodiment 19, wherein the washing in step (f) is performed with dichloromethane and/or acetone.

E21. The process according to any of embodiments 1-20, wherein said aqueous composition containing nalmefene hydrochloride and naltrexone, comprises a mother liquor obtained from a method of preparation of nalmefene hydrochloride dihydrate.

E22. The process according to embodiment 21, wherein said mother liquor is obtained from the re-slurry or the re-crystallization method disclosed in WO 2010/063292.

E23. The process according to any of embodiments 1-20, wherein said aqueous composition containing nalmefene hydrochloride and naltrexone, comprises a mother liquor obtained from a method of preparation of nalmefene hydrochloride monohydrate.

E24. The process according to any of embodiments 1-23, wherein said aqueous composition containing nalmefene hydrochloride and naltrexone, initially comprises naltrexone in an amount of less than 1% (by HPLC area) of the amount of nalmefene.

E25. The process according to any of embodiments 1-24, wherein said aqueous composition containing nalmefene hydrochloride and naltrexone initially comprises phosphorous by-products in an amount of less than 10% (by HPLC area) of the amount of nalmefene.

E26. The process according to any of embodiments 1-25, wherein the recovered nalmefene hydrochloride is at least 99% chemically pure.

E27. Nalmefene hydrochloride directly recovered from a process according to any of embodiments 1-26.

E28. The process according to any of embodiments 1-26, wherein the recovered nalmefene hydrochloride is further processed to nalmefene hydrochloride dihydrate or to nalmefene hydrochloride monohydrate.

E29. A process for the preparation of nalmefene hydrochloride dihydrate or nalmefene hydrochloride monohydrate, wherein said process includes recovering nalmefene hydrochloride by a process according to any of embodiments 1-26.

E30. Nalmefene hydrochloride dihydrate or nalmefene hydrochloride monohydrate directly obtained from a process according to any of embodiments 28-29.

E31. A pharmaceutical composition comprising nalmefene hydrochloride dihydrate or nalmefene hydrochloride monohydrate obtained from a process according to any of embodiments 28-29.

E32. A compound represented by the formula

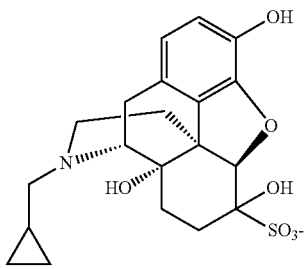

E33. The compound according to embodiment 32, wherein the compound is naltrexone bisulfite adduct.

EXAMPLES

The invention will be illustrated by the following non-limiting examples.

In the present context, chemical purity is measured by HPLC using the below conditions:

Column . . . Kinetex Phenomenex C18, 100×4.6 mm f.t 2.5 µm or equivalent
Mobile Phase A: . . . 1.1 g of Sodium Octansulfonate (FW 216.28) dissolved in 1 L of water, pH adjusted to 2.3 with diluted $H_3PO_4$
Mobile Phase B: . . . Acetonitrile
Mobile Phase C: . . . Water
Column temperature . . . 35° C.
Detector . . . UV at 230 nm
Injection volume . . . 10 µl
Flow . . . 1.2 mL/min
Time of analysis . . . 45 minutes

| Time (min) | MobilePhase A | MobilePhase B | MobilePhase C |
|---|---|---|---|
| 0 | 80 | 20 | 0 |
| 30 | 60 | 40 | 0 |
| 45 | 20 | 80 | 0 |
| 46 | 0 | 10 | 90 |
| 50 | 0 | 10 | 90 |
| 55 | 80 | 20 | 0 |
| 60 | 80 | 20 | 0 |

Example 1

Recovery of Nalmefene Hydrochloride from Aqueous Solution

Nalmefene HCl aqueous mother liquor (400 g); containing about 36 g of "residue of evaporation" with the following composition (% by HPLC area): nalmefene 92.08%, naltrexone 0.49%, methyldiphenylphosphine oxide 0.77%, triphenylphosphineoxide 4.0%; was treated with 0.34 g of sodium bisulfite and concentrated under vacuum distilling 323 g of solvent. The concentrated mixture was cooled down to 0° C. and maintained at this temperature overnight. The solid was filtered and washed with acetone (34 mL) obtaining 21 g of nalmefene HCl. HPLC analysis (% by area): nalmefene 98.92%, naltrexone 0.09%, methyldiphenylphosphine oxide 0.04%, triphenylphosphineoxide 0.16%.

Example 2

Recovery of Nalmefene Hydrochloride from Aqueous Solution (Including Extraction with Organic Solvent)

Nalmefene HCl aqueous mother liquor (400 g); containing about 36 g of "residue of evaporation" with the following composition (% by HPLC area): nalmefene 92.08%, naltrexone 0.49%, methyldiphenylphosphine oxide 0.8%, triphenylphosphineoxide 4.0%; was extracted with dichloromethane (2*50 mL). The aqueous layer was then concentrated under vacuum obtaining a suspension. Sodium bisulfite (0.3 g) was charged and the mixture was maintained at 60-65° C. for three hours. The suspension was cooled down to 0-5° C. and the solid was filtered and washed with dichloromethane (50 mL) and acetone (about 30 mL) obtaining 28 g of nalmefene HCl. HPLC analysis (% by area): nalmefene 99.36%, naltrexone 0.12%. Methyldiphenylphosphine oxide and triphenylphosphineoxide below detection limit.

Example 3

Recovery of Nalmefene Hydrochloride from Aqueous Solution (Including Extraction with Organic Solvent)

Nalmefene HCl aqueous mother liquor (145 kg); containing about 16 kg of "residue of evaporation", with the following composition (% by HPLC area): nalmefene 90.97, naltrexone 0.23%, methyldiphenylphosphine oxide 1.1%, triphenylphosphineoxide 4.9%; was extracted with dichloromethane (2*30 L). The aqueous layer was then concentrated under vacuum distilling 128 kg of solvent. The suspension was diluted with water (7 kg). Sodium bisulfite 0.15 kg was added and the mixture maintained at 60-65° C. for four hours. The suspension was cooled to 0-5° C. and stirred for four hours. The solid was filtered and washed with dichloromethane (15 L) and acetone (15 L) obtaining 12.8 kg of nalmefene HCl. HPLC analysis (% by area): nalmefene 99.12%, naltrexone 0.05%. Methyldiphenylphosphine oxide and triphenylphosphineoxide below detection limit.

Example 4

Comparative Example (No Addition of Bisulfite Salt, No Extraction with Organic Solvent)

Nalmefene HCl aqueous mother liquor (400 g); containing about 44 g of "residue of evaporation" with the following composition (% by HPLC area): nalmefene 92.08%, naltrexone 0.49%, methyldiphenylphosphine oxide 0.77%, triphenylphosphineoxide 4.0%; was concentrated under vacuum distilling 323 g of solvent. The concentrated mixture was cooled down to 0° C. and maintained at this temperature overnight. The solid was filtered and washed with acetone (34 mL) obtaining 28.5 g of nalmefene HCl. HPLC analysis (% by area): nalmefene 97.42%, naltrexone 0.24%, methyldiphenylphosphine oxide 0.06%, triphenylphosphineoxide 1.9%.

Comparison of the data from Example 4 with the data from Examples 1-3 clearly demonstrates that the amount of naltrexone in the end product is efficiently reduced by the process of the invention. Examples 2 and 3 furthermore show that the amount of methyldiphenylphosphine oxide and triphenylphosphineoxide is reduced by extraction with organic solvent.

The invention claimed is:
1. A process for recovery of nalmefene hydrochloride from an aqueous composition containing nalmefene hydrochloride and naltrexone, said process comprising the step of isolating nalmefene hydrochloride from an aqueous suspension comprising naltrexone bisulfite adduct and solid nalmefene hydrochloride.
2. The process according to claim 1, wherein said aqueous composition is an aqueous solution.
3. A process according to claim 1 comprising the following steps:
(b) concentrating the aqueous composition;
(c) mixing the aqueous composition with a bisulfite salt or with a suitable salt generating the bisulfite anion in an aqueous medium,
wherein steps (b) and (c) can be performed simultaneously and/or sequentially in any order;
(d) cooling the mixture obtained from steps (b) and (c); and
(e) isolating the solid from the mixture obtained in step (d) to obtain nalmefene hydrochloride.
4. The process according to claim 3, wherein steps (b) and (c) are performed simultaneously.
5. The process according to claim 3, wherein steps (b) and (c) are performed sequentially starting with step (c) followed by step (b).
6. The process according to claim 3, wherein steps (b) and (c) are performed sequentially starting with step (b) followed by step (c).
7. The process according to claim 3, comprising the initial step (a) which is performed prior to steps (b) and (c)
(a) extracting the aqueous composition with an organic solvent followed by isolation of the aqueous layer;
wherein the aqueous composition of step (b) or (c) comprises the aqueous layer isolated from step (a).
8. The process according to claim 7, wherein the organic solvent in step (a) is dichloromethane.
9. The process according to claim 3, wherein the concentration in step (b) is performed by vacuum distillation.
10. The process according to claim 3, wherein the bisulfite salt in step (c) is sodium bisulfite.
11. The process according to claim 3, followed by the step;
(f) washing the solid obtained in step (e) with one or more suitable organic solvents.
12. The process according to claim 1, wherein said aqueous composition containing nalmefene hydrochloride and naltrexone, comprises a mother liquor obtained from a method of preparation of nalmefene hydrochloride dihydrate.
13. The process according to claim 1, wherein said aqueous composition containing nalmefene hydrochloride and naltrexone, comprises a mother liquor obtained from a method of preparation of nalmefene hydrochloride monohydrate.
14. A process for the preparation of nalmefene hydrochloride dihydrate or nalmefene hydrochloride monohydrate, wherein said process includes recovering nalmefene hydrochloride by a process according to claim 1.
15. A compound represented by the formula

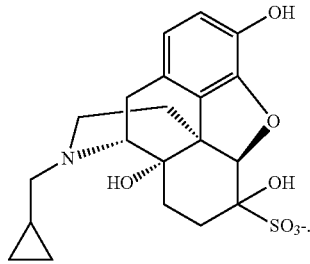

16. The process according to claim 4, comprising the initial step (a) which is performed prior to steps (b) and (c)
(a) extracting the aqueous composition with an organic solvent followed by isolation of the aqueous layer;
wherein the aqueous composition of step (b) or (c) comprises the aqueous layer isolated from step (a).
17. The process according to claim 5, comprising the initial step (a) which is performed prior to steps (b) and (c)
(a) extracting the aqueous composition with an organic solvent followed by isolation of the aqueous layer;
wherein the aqueous composition of step (b) or (c) comprises the aqueous layer isolated from step (a).

18. The process according to claim 6, comprising the initial step (a) which is performed prior to steps (b) and (c)
  (a) extracting the aqueous composition with an organic solvent followed by isolation of the aqueous layer;
  wherein the aqueous composition of step (b) or (c) comprises the aqueous layer isolated from step (a).

19. A process for the preparation of nalmefene hydrochloride dihydrate or nalmefene hydrochloride monohydrate, wherein said process includes recovering nalmefene hydrochloride by a process according to claim 3.

* * * * *